United States Patent
Murase (10) Patent No.: US 8,985,772 B2
(45) Date of Patent: Mar. 24, 2015

(54) OPHTHALMOLOGIC PHOTOGRAPHING APPARATUS AND OPHTHALMOLOGIC PHOTOGRAPHING METHOD

(71) Applicant: Nidek Co., Ltd., Aichi (JP)

(72) Inventor: Yuji Murase, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 14/058,438

(22) Filed: Oct. 21, 2013

(65) Prior Publication Data

US 2014/0111767 A1    Apr. 24, 2014

(30) Foreign Application Priority Data

Oct. 24, 2012  (JP) ................................. 2012-235182

(51) Int. Cl.
    *A61B 3/14*    (2006.01)
    *A61B 3/10*    (2006.01)
    *A61B 3/00*    (2006.01)

(52) U.S. Cl.
    CPC ............... *A61B 3/102* (2013.01); *A61B 3/0058* (2013.01); *A61B 3/14* (2013.01)
    USPC ............................. 351/206; 351/210; 351/211

(58) Field of Classification Search
    USPC ................................................. 351/200–246
    See application file for complete search history.

(56) References Cited

U.S. PATENT DOCUMENTS

| | | | |
|---|---|---|---|
| 2008/0024721 A1 | 1/2008 | Ueno et al. | |
| 2011/0051088 A1* | 3/2011 | Shimizu et al. | 351/206 |
| 2011/0170062 A1 | 7/2011 | Isogai et al. | |
| 2012/0127428 A1 | 5/2012 | Isogai et al. | |
| 2012/0249956 A1* | 10/2012 | Narasimha-Iyer et al. | 351/206 |
| 2013/0229623 A1* | 9/2013 | Murase | 351/206 |

FOREIGN PATENT DOCUMENTS

| | | |
|---|---|---|
| JP | 2008-029467 | 2/2008 |
| JP | 2011-092702 | 5/2011 |
| JP | 2011-245183 | 12/2011 |

* cited by examiner

*Primary Examiner* — Mohammed Hasan
(74) *Attorney, Agent, or Firm* — Rankin, Hill & Clark LLP (57) ABSTRACT

An ophthalmologic photographing apparatus includes: an optical coherence system for obtaining a tomographic image of an examinee's eye, having an optical scanner for scanning the eye with measurement light and a detector for detecting an interference signal of the light and reference light; an observing optical system for acquiring a front image of the eye; a scan controller for controlling the optical scanner to scan with the light different transverse positions set on the image, and acquire first interference signals at the positions; a display controller for displaying on a monitor an image created in response to the first interference signal; and an image recapture setting unit for setting a rephotographing transverse position in response to an operation signal from an operating unit for the image on the monitor. The scan controller scans the eye with the light at the rephotographing transverse position, and acquires a second interference signal.

8 Claims, 5 Drawing Sheets

OPHTHALMOLOGIC PHOTOGRAPHING APPARATUS AND OPHTHALMOLOGIC PHOTOGRAPHING METHOD

CROSS-REFERENCE TO RELATED APPLICATION

This application is based on Japanese Patent Application No. 2012-235182 filed with the Japan Patent Office on Oct. 24, 2012, the entire content of which is hereby incorporated by reference.

BACKGROUND

1. Technical Field

The present disclosure relates to an ophthalmologic photographing apparatus, an ophthalmologic photographing method, and a recording medium where an ophthalmologic photographing program is recorded, which are for capturing a tomographic image of an examinee's eye.

2. Related Art

An ophthalmic optical coherence tomography (OCT) apparatus using low coherent light is known as an ophthalmologic photographing apparatus that can obtain a tomographic image of a predetermined portion (e.g., the fundus or anterior segment) of an examinee's eye noninvasively (e.g., JP-A-2008-29467).

Moreover, known as an ophthalmologic optical coherence tomography is an apparatus that acquires a tomographic image using a scan pattern formed of a combination of scans at different transverse positions (a plurality of scans) (for example, a raster scan, a radial scan, or a multi-scan). The apparatus acquires a plurality of tomographic images in a single capture (see, for example, JP-A-2011-92702 and JP-A-2011-245183).

SUMMARY

An ophthalmologic photographing apparatus includes: an optical coherence system configured to obtain a tomographic image of an examinee's eye, including an optical scanner configured to scan the examinee's eye with measurement light and a detector configured to detect an interference signal of the measurement light and reference light; an observing optical system configured to acquire a front image of the examinee's eye; a scan controller configured to control the optical scanner to scan with the measurement light a plurality of different transverse positions set on the front image, and acquire first interference signals at the respective transverse positions; a display controller configured to display on a monitor an image created in response to the first interference signal; and an image recapture setting unit configured to set a rephotographing transverse position in response to an operation signal from an operating unit for the image on the monitor. The scan controller scans the examinee's eye with the measurement light at the rephotographing transverse position to acquire a second interference signal.

DETAILED DESCRIPTION

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

When a tomographic image is captured using a scan pattern formed of a combination of a plurality of scans, it takes some time from the start of image capture to the end of all the scans. Hence, the fixation shift, blink, and/or the like of an examinee's eye may occur during image capture. In this case, a scan that fails in image capture arises during the plurality of scans.

In such a case, image capture is performed again (hereinafter, referred to as "image recapture"). The image recapture is performed for all the plurality of scans, causing an examiner (user) to spend much time and labor. Moreover, even if image recapture is performed, the fixation shift, blink, and/or the like of the examinee's eye may occur again during image recapture. In this case, image capture of the examinee's eye fails repeatedly.

An object of the present disclosure is to provide an ophthalmologic photographing apparatus that can shorten the time for image recapture as well as easily capture a tomographic image.

An ophthalmologic photographing apparatus includes: an optical coherence system configured to obtain a tomographic image of an examinee's eye, including an optical scanner configured to scan the examinee's eye with measurement light and a detector configured to detect an interference signal of the measurement light and reference light; an observing optical system configured to acquire a front image of the examinee's eye; a scan controller configured to control the optical scanner to scan with the measurement light a plurality of different transverse positions set on the front image, and acquire first interference signals at the respective transverse positions; a display controller configured to display on a monitor an image created in response to the first interference signal; and an image recapture setting unit configured to set a rephotographing transverse position in response to an operation signal from an operating unit for the image on the monitor. The scan controller scans the examinee's eye with the measurement light at the rephotographing transverse position to acquire a second interference signal.

The ophthalmologic photographing apparatus can shorten the time for image recapture as well as easily capture a tomographic image.

Figure 1:
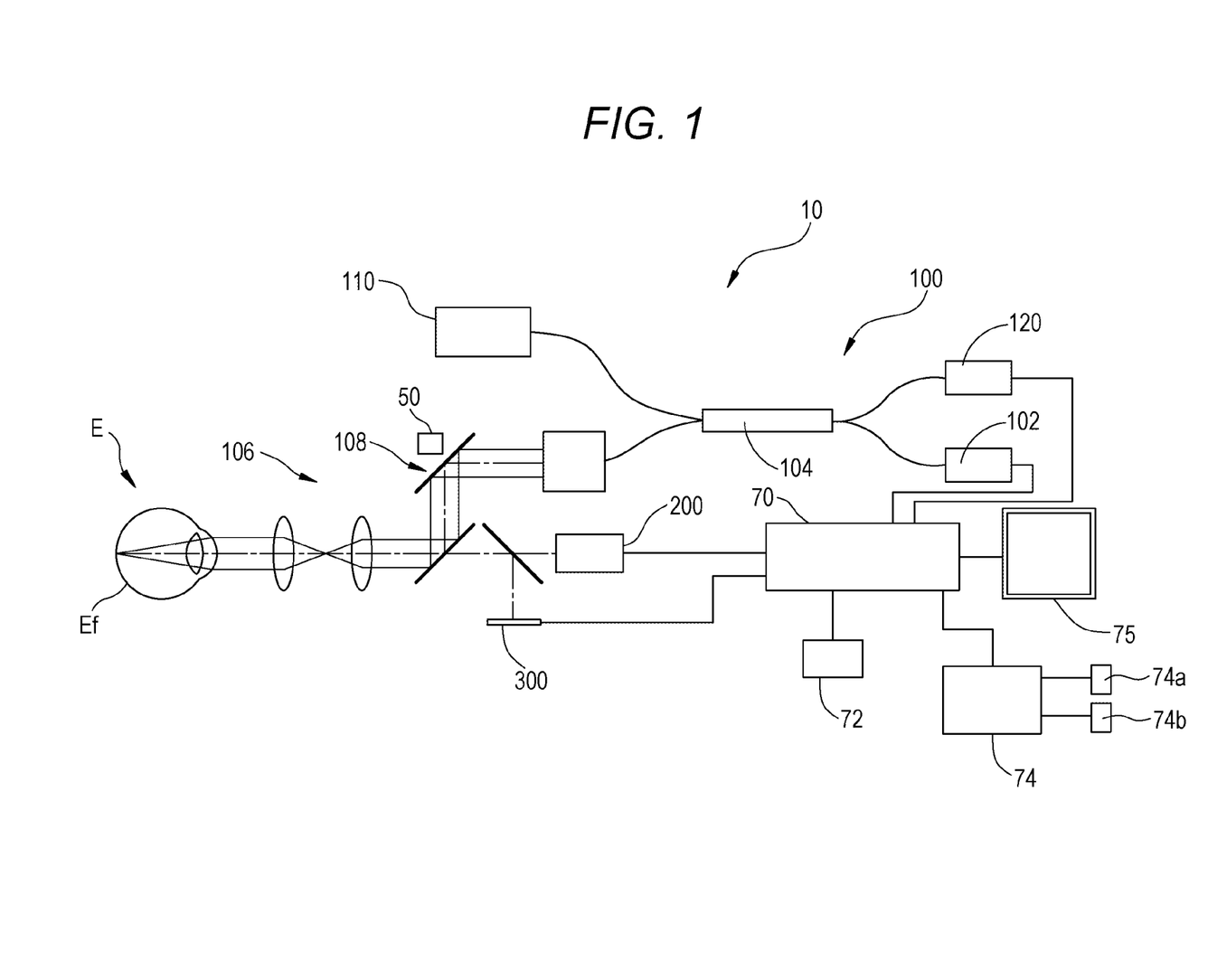
FIG. 1 is a schematic diagram illustrating the configuration of an ophthalmologic photographing apparatus according to an embodiment.

A description will hereinafter be given of the ophthalmologic photographing apparatus according to the embodiment with reference to the drawings. FIG. 1 is a schematic block diagram illustrating the configuration of the ophthalmologic photographing apparatus according to the embodiment. In the embodiment, the axis direction of an examinee's eye (eye E) is set to be a Z direction, the horizontal direction to be an X direction, and the vertical direction to be a Y direction. Therefore, the surface direction of the fundus is the X-Y direction.

<Outline>

A description will be given of the outline of the ophthalmologic photographing apparatus according to the embodiment. An ophthalmologic photographing apparatus (optical coherence tomography device) 10 according to the embodiment includes an optical coherence system (OCT optical system) 100, an observing optical system 200, a display unit (monitor) 75, an operation input unit (operating unit) 74, and a control unit (CPU) 70.

The optical coherence system 100 has a scanning unit (optical scanner) 108, and a detector 120, and obtains a tomographic image of the examinee's eye. The optical scanner 108 scans the examinee's eye two-dimensionally with light emitted from a light source 102. The detector 120 detects a coherent state of measurement light emitted from the light source, and reference light.

The observing optical system 200 acquires a front image (frontal image) of the examinee's eye as a moving image. The observing optical system 200 has a light-receiving device. The light-receiving device receives, for example, reflected infrared light irradiating the examinee's eye, from the examinee's eye. The observing optical system 200 may obtain a front image of the examinee's eye in response to a light-receiving signal from the light-receiving device. The observing optical system 200 includes, for example, an SLO or fundus camera. Moreover, the observing optical system 200 may also serve as the optical coherence system 100. In this case, a front image of the examinee's eye is acquired based on a three-dimensional image acquired by the optical coherence system 100.

If the observing optical system 200 is an SLO or fundus camera, the control unit 70 aligns the positions of a front image acquired by the observing optical system 200 and a front image acquired by the optical coherence system 100) (performs matching). The front image is, for example, an OCT front image (e.g., an integral image) based on the three-dimensional image data. Consequently, the tomographic image acquired by the optical coherence system 100 is brought into correspondence with the front image acquired by the observing optical system 200.

The operating unit 74 is operated by the examiner. The operating unit 74 may be, for example, a user interface such as a mouse 74a, a trackball, or a touchscreen.

The monitor 75 may be, for example, a display on a PC, or a display on the ophthalmologic photographing apparatus. The monitor 75 may be a touchscreen. If the monitor 75 is a touchscreen, the monitor 75 also functions as an operating unit.

In the embodiment, the control unit 70 also serves as a scan controller, a display controller, and an image recapture setter, but not limited thereto. Alternatively, the control unit 70 may be provided as individually different controllers, or part of the controllers may also serve as another controller.

<Control Operation>

The control unit 70 controls the optical scanner 108 at a plurality of different transverse positions (photographing positions) set on a front image of the examinee's eye. The control unit 70 scans the examinee's eye with the measurement light to acquire interference signals (first interference signals) at the respective transverse positions. The control unit 70 displays on the monitor 75 images created in response to the interference signals acquired at the transverse positions. The control unit 70 sets at least one or more rephotographing transverse positions in response to an operation signal from the operating unit 74 for the images created in response to the acquired interference signals on the monitor 75. The control unit 70 scans the examinee's eye with the measurement light at the set rephotographing transverse position to acquire an interference signal (second interference signal).

For example, there are various scan patterns as scans for image capture at the plurality of different transverse positions. For example, these scans include a multi-scan, a radial scan, a raster scan, and a cross scan. Moreover, there is also a scan pattern formed of a combination of a line scan, a circle scan, and the like.

Images to be created in response to the interference signals include, for example, a front image and a tomographic image. In this case, for example, the monitor 75 displays at least one of the front image and the tomographic image.

The examiner may set the rephotographing transverse position from the front or tomographic image created in response to the interference signal. Alternatively, the examiner may set the rephotographing transverse positions from image capture information acquired in response to the interference signal. Examples of the image capture information include the number of tomographic images used in an averaging process performed on the tomographic images of each different transverse position (scan line), the brightness distribution of a tomographic image, and a layer detection result.

Moreover, an image in a still state is used for the image to be created in response to the interference signal, for example, at the time of setting the rephotographing transverse position. For example, if tomographic images are used as the images in the still state, the examiner checks the tomographic images in the still state on the monitor 75 and selects the tomographic image to be recaptured. The examiner operates the operating unit 74 to transmit an operation signal related to the selected tomographic image to the control unit 70. Based on this operation signal, the control unit 70 sets a transverse position (photographing position) on the front image with reference to the tomographic image selected in response to the operation signal from the operating unit 74, as the rephotographing transverse position for the tomographic image in the still state on the monitor 75. In this manner, the examiner can check the tomographic images at the transverse positions and set the rephotographing position. Hence, the examiner can select only a tomographic image of a desired photographing position as an image recapture target. Hence, the ophthalmologic photographing apparatus 10 has high convenience. Moreover, the tomographic images are checked and then image recapture is performed. Accordingly, the photographing position where image capture could not been performed well can be appropriately selected as the rephotographing position.

In image recapture, the control unit 70 performs tracking control. For example, the control unit 70 detects by image processing a displacement between a first front image of the examinee's eye and a second front image of the examinee's eye. The first front image of the examinee's eye is acquired by the observing optical system 200 when the interference signals are acquired at the plurality of different transverse positions. The second front image of the examinee's eye is acquired by the observing optical system 200 when the interference signal is acquired at the rephotographing transverse position. The control unit 70 controls the drive of the optical scanner 108 based on the result of the detected displacement and reacquires the interference signal at the rephotographing transverse position.

For example, image recapture is set on a check screen for checking a tomographic image captured. The display on the monitor 75 can be switched between an image capture screen for acquiring an interference signal and the check screen for checking the acquired interference signal. For example, the control unit 70 switches and displays either of the image capture screen and the check screen on the monitor 75 in a series of image capture operations.

For example, on the image capture screen, the control unit 70 controls the optical scanner 108 at the plurality of different transverse positions of the examinee's eye, which are set on the front image, and scans the examinee's eye with the measurement light. Consequently, the control unit 70 acquires the interference signals at the respective transverse positions. Next, the control unit 70 switches the display on the monitor 75 from the image capture screen to the check screen. The control unit 70 displays on the monitor 75 images created based on the acquired interference signals at the respective transverse positions. The control unit 70 sets at least one or more rephotographing transverse positions on the check screen in response to an operation signal from the operating unit 74, for the images on the monitor 75.

Next, the control unit 70 switches the display on the monitor 75 from the check screen to the image capture screen. The control unit 70 then scans the examinee's eye with the measurement light at the set rephotographing transverse position to acquire an interference signal. For example, the control unit 70 controls the optical scanner 108 on the image capture screen and scans the examinee's eye with the measurement light in the transverse direction at a scan position preset as the rephotographing transverse position. The control unit 70 may acquire a tomographic image at the rephotographing transverse position as a still image in response to a photographing start signal generated automatically or manually.

In such a configuration, image recapture can be performed immediately after an image capture at a photographing position where an unexcellent tomographic image out of a plurality of the captured tomographic images was acquired. Hence, image recapture can be performed smoothly without time and trouble.

Moreover, the control unit 70 may display the image capture screen and the check screen in different areas on the same screen on the monitor 75. Other than this, the image capture screen and the check screen may be displayed on the same screen and switched by switching their sizes.

The control unit 70 may execute at least any of the tracking control of the measurement light and the adjustment of an optical path length in accordance with the movement of the examinee's eye, in a state where the check screen is being displayed on the monitor 75. Consequently, image recapture is performed smoothly. The control unit 70 may stop the application of the measurement light while the conformation screen is being displayed on the monitor 75. Consequently, the burden on the examinee's eye is reduced. After the image recapture, for example, the control unit 70 replaces the interference signal acquired at the transverse position selected (set) for the image before the image recapture on the monitor 75 (the interference signal before the image recapture, which was acquired at the rephotographing transverse position (the first interference signal)) with the interference signal acquired by the image recapture at the rephotographing transverse position (the second interference signal). Moreover, for example, the control unit 70 may add and average the interference signal acquired at the transverse position selected (set) in response to the operation signal from the operating unit 74 for the image before the image recapture on the monitor 75 and the interference signal acquired by the image recapture at the rephotographing transverse position. Consequently, the control unit 70 can change all the tomographic images acquired at the plurality of different transverse positions to excellent tomographic images. Consequently, image capture that uses a scan pattern related to a plurality of different transverse positions can be performed smoothly without time and trouble.

For example, a front image acquired at the start of image capture can be used as the first front image. It is sufficient if the first front image is a front image acquired prior to the second front image. For example, the control unit 70 may update (set) the first front image so as to set a front image acquired immediately prior to a newly acquired front image as the first front image, whenever a front image is acquired.

For example, a current front image acquired in real time can be used as the second front image.

The configuration or operation of the embodiment is not limited to the above-mentioned aspect. For example, ophthalmologic photographing software (program) that executes the functions of the embodiment may be provided to an ophthalmologic photographing system or an ophthalmologic photographing apparatus via a network or various recording media (for example, a memory 72 (described below). A computer (for example, a CPU) of the ophthalmologic photographing system or the ophthalmologic photographing apparatus can also read and execute the program.

For example, cited is an ophthalmologic photographing program to be executed in a control apparatus that controls the operation of the ophthalmologic photographing apparatus 10 provided with the optical coherence system 100) configured to obtain a tomographic image of an examinee's eye, including the optical scanner 108 configured to scan the examinee's eye with measurement light emitted from the light source, and the detector 120 configured to detect an interference signal of the measurement light and reference light, which are emitted from the light source, and the observing optical system 200 configured to acquire a front image of the examinee's eye. In this case, the ophthalmologic photographing program is executed by a processor (for example, the control unit 70) of the control apparatus. The processor of the control apparatus executes a control step of controlling the optical scanner 108 at a plurality of different transverse positions of the examinee's eye set on a front image acquired by the observing optical system 200, scanning the examinee's eye with the measurement light, and acquiring interference signals (first interference signals) at the transverse positions, a display control step of displaying on the monitor 75 an image created in response to the interference signal (first interference signal), an image recapture setting step of setting at least one or more rephotographing transverse positions in response to an operation signal from the operating unit 74 for the images on the monitor 75, and an image recapture control step of scanning the examinee's eye with the measurement light at the rephotographing transverse position and acquiring an interference signal (second interference signal).

Example

Hereinafter, an example of the embodiment is described with reference to the drawings. FIG. 1 is a schematic block diagram illustrating the configuration of an ophthalmologic photographing apparatus according to the example. The following description will be given of a fundus photographing apparatus (the apparatus) that photographs the fundus of the examinee's eye as an example of the ophthalmologic photographing apparatus. The ophthalmologic photographing apparatus is not limited to a fundus photographing apparatus. The ophthalmologic photographing apparatus includes an anterior segment photographing apparatus that photographs the anterior segment of the examinee's eye.

Here, the schematic configuration of the apparatus is described. The apparatus is the optical coherence tomography device (OCT device) 10 for photographing a tomographic image of a fundus Ef of the examinee's eye E. The OCT device 10 includes the optical coherence system (OCT optical system) 100, the frontal-view observing optical system 200, a fixation target projecting unit 300, and the arithmetic controller (CPU) 70.

The OCT optical system 100 irradiates the fundus with measurement light. The OCT optical system 100 detects the coherent state of the measurement light reflected by the fundus and reference light by the light-receiving device (the detector 120). The OCT optical system 100) includes an irradiation position-changing unit (e.g., the optical scanner 108 and the fixation target projecting unit 300) that changes the irradiation position of the measurement light on the fundus Ef in order to change a capturing position on the fundus Ef. The control unit 70 controls the operation of the irradiation position-changing unit based on the set capturing position information. The control unit 70 acquires a tomographic image in response to a light-receiving signal from the detector 120.

<OCT Optical System>

The OCT optical system 100 is configured as a so-called an ophthalmic optical coherence tomography (OCT) apparatus, and captures a tomographic image of the eye E. The OCT optical system 100 allows a coupler (light splitter) 104 to split light emitted from the measurement light source 102 into measurement light (sample light) and reference light. The OCT optical system 100 allows a measuring optical system 106 to lead the measurement light to the fundus Ef of the eye E. Moreover, the OCT optical system 100 leads the reference light to a reference optical system 110. Coherent light obtained by combining the measurement light reflected by the fundus Ef and the reference light is subsequently received by the detector (light-receiving device) 120.

The detector 120 detects the coherent state of the measurement light and the reference light. In Fourier domain OCT, the spectral intensity of the coherent light is detected by the detector 120. The spectral intensity data is Fourier transformed to acquire a depth profile (A-scan signal) in a predetermined range. Fourier domain OCT includes, for example, Spectral-domain OCT (SD-OCT), Swept-source OCT (SS-OCT), and Time-domain OCT (TD-OCT).

The optical scanner 108 scans the fundus of the examinee's eye with light from the measurement light source. For example, the optical scanner 108 scans the fundus two-dimensionally (in the X-Y direction (transverse direction)) with the measurement light. The optical scanner 108 is disposed at a position that is substantially conjugated with the pupil. The optical scanner 108 has two galvanometer mirrors, for example. The reflection angles of these galvanometer mirrors are arbitrarily adjusted by a drive mechanism 50.

Consequently, it becomes possible to change a reflection (travel) direction of light flux emitted from the light source 102. Therefore, it is possible to scan the fundus in an arbitrary direction with the measurement light. Consequently, it becomes possible to change the capturing position on the fundus Ef. It is sufficient if the optical scanner 108 is configured to deflect light. A reflective mirror (a galvanometer mirror, polygon mirror, or resonant scanner), an acousto-optic modulator (AOM) that changes the travel (deflection) direction of light, or the like is used as the optical scanner 108.

The reference optical system 110 generates reference light to be combined with reflected light acquired by the reflection of the measurement light from the fundus Ef. The reference optical system 110 may be the Michelson system or Mach-Zehnder system. The reference optical system 110 includes, for example, a catoptric system (e.g., a reference mirror). The reference optical system 110 causes the catoptric system to reflect light from the coupler 104 to return the light to the coupler 104 again and leads it to the detector 120. In another example, the reference optical system 110 includes a transmission optical system (e.g., an optical fiber). The reference optical system 110 does not return the light from the coupler 104 but allows the light to pass therethrough and accordingly leads the light to the detector 120.

The reference optical system 110 includes a member for changing a difference in optical path length between measurement light and reference light by moving an optical member on a reference optical path. In the reference optical system 110, the reference mirror is moved in the optical axis direction, for example. A member to change the difference in optical path length may be disposed on a measurement optical path of the measuring optical system 106.

<Frontal-View Observing Optical System>

The frontal-view observing optical system (front image observing device) 200 is provided to obtain a front image of the fundus Ef. The observing optical system 200 has a device configuration of what is called an ophthalmic scanning laser ophthalmoscope (SLO), for example. The observing optical system 200 includes, for example, an optical scanner and a second light-receiving device. The optical scanner scans the fundus two-dimensionally with measurement light (e.g., infrared light) emitted from a light source. The second light-receiving device receives fundus reflected light via a confocal opening disposed at a position that is substantially conjugated with the fundus.

The observing optical system 200) may have the configuration of what is called a fundus camera type. Moreover, the OCT optical system 100 may also serve as the observing optical system 200. In other words, a front image may be acquired using data forming a tomographic image, the data being obtained two-dimensionally. The data include, for example, an integral image in a depth direction of a three-dimensional tomographic image, an integrated value of spectral data at the positions of X and Y, or luminance data at the positions of X and Y in a certain depth direction, and a retinal surface layer image.

<Fixation Target Projecting Unit>

The fixation target projecting unit 300 includes an optical system for guiding a direction of the visual line of the eye E. The projecting unit 300 includes a fixation target to be presented to (projected on) the eye E, and can guide the visual line of the eye E to a plurality of directions.

For example, the fixation target projecting unit 300 includes a visible light source that emits visible light, and changes a position to present the target two-dimensionally. If the direction of the visual line is changed accordingly, it leads to a change in capturing position. For example, if the fixation target is presented from the same direction as the photographing optical axis, the center portion of the fundus is set as a photographed portion. Moreover, if the fixation target is presented above the photographing optical axis, the upper part of the fundus is set as a photographed portion. In other words, a photographing portion is changed in accordance with the position of the target relative to the photographing optical axis.

Cited as the fixation target projecting unit 300 are, for example, a configuration to adjust a fixation position by adjusting the lighting state of a plurality of LEDs arranged in a matrix fashion, and a configuration to adjust a fixation position by combining a scan by an optical scanner using the light of a light source and control over the lighting up and out of the light source. Moreover, the projecting unit 300 may be an internal or external fixation light type.

<Controller>

The control unit 70 controls the entire apparatus including the members 100 to 300. Moreover, the control unit 70 also serves as an image processor that processes an image acquired, an image analyzer that analyzes an image acquired, and the like. The control unit 70 is implemented by a general CPU (Central Processing Unit), and the like. The control unit 70 analyzes the fundus Ef based on a tomographic image as indicated below.

The control unit 70 acquires a tomographic image by performing image processing on a light-receiving signal output from the detector 120 of the OCT optical system 100. Furthermore, the control unit 70 acquires a front image in response to a light-receiving signal output from the light-receiving device of the frontal-view observing optical system 200. Moreover, the control unit 70 controls the fixation target projecting unit 300 to change a fixation position.

The memory (storage unit) 72, the monitor 75, and the control unit (operating unit) 74 are electrically connected to the control unit 70, respectively. The control unit 70 controls a display screen of the monitor 75. An acquired fundus image is output to the monitor 75 as a still image or moving image as well as is stored in the memory 72. For example, a photographed tomographic image (e.g., a three-dimensional tomographic image), a front image, and various kinds of information on photographing such as the capturing position information of the tomographic image are recorded in the memory 72. The memory 72 stores a control program (ophthalmologic photographing program) for controlling the operation of the present apparatus (ophthalmologic photographing apparatus 10). The control unit 70 controls the OCT optical system 100, the frontal-view observing optical system 200, and the fixation target projecting unit 300, in response to an operation signal output from the operating unit 74. The operating unit 74 is connected to the mouse 74a, an operation knob 74b, an operation knob 74c, and the like as operating members to be operated by the examiner.

The mouse 74a has a sensor, two left and right mouse buttons, and a wheel mechanism. The sensor detects a movement signal output from a main body of the mouse 74a that is moved two-dimensionally by a hand of the examiner. The mouse buttons detect a press by the hand of the examiner. The wheel mechanism is disposed between the two left and right mouse buttons. The wheel mechanism can rotate in the front and back direction.

The operation knobs 74b and 74c can rotate in the left and right direction.

The monitor 75 may be a display monitor mounted on the apparatus body, or a display monitor of a personal computer, or include both of them.

<Control Operation>

Figure 2:
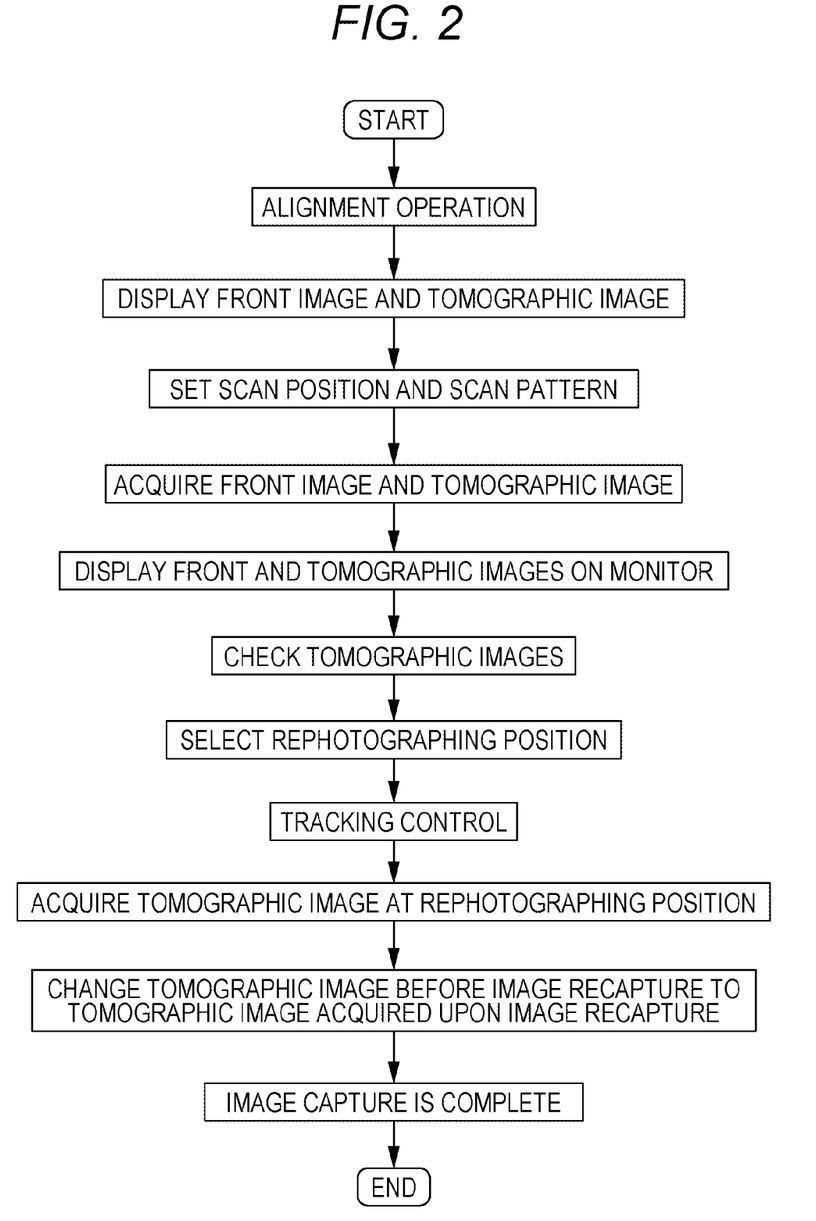
FIG. 2 is a flowchart illustrating the flow of control operation.

A description will be given of the control operation of the apparatus including the above configuration. FIG. 2 illustrates the flow of control operation of the present apparatus. The control unit 70 executes the process shown in FIG. 2 in accordance with the control program stored in the memory 72. The examiner instructs the examinee to fix his/her eye on the fixation target of the fixation target projecting unit 300. The examiner subsequently performs an alignment operation using the operating unit 74 (for example, an unillustrated joystick) so as to locate the measurement optical axis on the pupil center of the examinee's eye while watching on the monitor 75 an anterior segment observation image captured by a camera (not shown) for anterior segment observation.

The control unit 70 then controls the optical scanner 108 to scan the fundus with measurement light in a predetermined direction. The control unit 70 acquires a light-receiving signal corresponding to a predetermined scan area from an output signal output from the detector 120 during the scan. The control unit 70 forms a tomographic image in response to the light-receiving signal. The control unit 70 controls the OCT optical system 100 to acquire the tomographic image. Furthermore, the control unit 70 controls the observing optical system 200 to acquire a fundus front image. The control unit 70 then at any time acquires the tomographic image (front image) from the OCT optical system 100 and the fundus front image from the observing optical system 200.

In the embodiment, a scan pattern formed of a combination of a plurality of scans at different transverse positions is used to acquire tomographic images. In the following description, a description will be given taking a multi-scan as an example of the scan pattern. Scan lines of the multi-scan of the embodiment include, for example, a total of 10 scan lines of five lines in the longitudinal direction and five lines in the lateral direction. Naturally, the number of scan lines is not limited to this but can be changed. The present disclosure is not limited only to the application to a multi-scan. The present disclosure can be applied as long as the scan pattern is the one formed of a combination of a plurality of scans at different transverse positions. The present disclosure can also be applied to, for example, a raster scan, a radial scan, and a cross scan.

Figure 3:
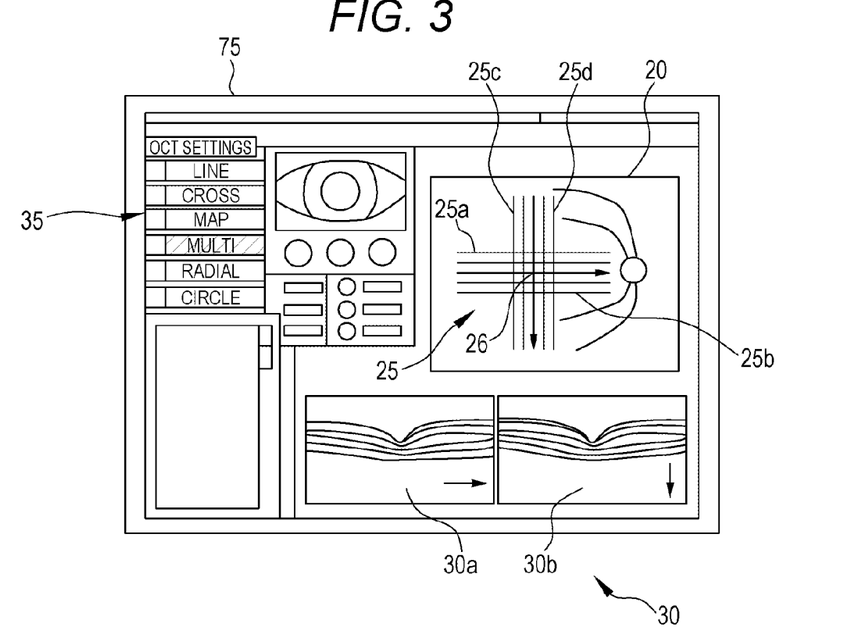
FIG. 3 is an exemplary diagram illustrating an image capture screen to be displayed on a monitor at the time of image capture by a multi-scan.

FIG. 3 is an exemplary diagram illustrating the image capture screen to be displayed on the monitor 75 at the time of image capture by a multi-scan. The control unit 70 displays on the monitor 75 a front image 20, a target (line) 25, and a tomographic image 30, which have been acquired by the observing optical system 200. The target 25 is a target representing a measurement position (photographing position) and scan pattern of a tomographic image on the front image 20. In other words, if the scan pattern is changed, the control unit 70 changes a display pattern of the target based on the changed scan pattern. The target 25 is electrically superimposed and displayed on the front image on the monitor 75.

For example, a first tomographic image 30a and a second tomographic image 30b are displayed as the tomographic image 30 on the monitor 75. The first tomographic image 30a represents, for example, a tomographic image acquired at a sectioning position that passes across the target 25 in the lateral direction (X direction). Moreover, the second tomographic image 30b represents, for example, a tomographic image acquired at a sectioning position that passes across the target 25 in the longitudinal direction (Y direction).

In the embodiment, tomographic images displayed in the first tomographic image 30a and the second tomographic image 30b on the image capture screen as an initial setting at the time of image capture by a multi-scan are tomographic images at a center position 26 of the multi-scan, which are of a scan in the lateral direction (a first tomographic image) and of a scan in the longitudinal direction (a second tomographic image). Naturally, images at different scan positions may be displayed at the time of image capture. Moreover, tomographic images displayed in the first tomographic image 30a and the second tomographic image 30b can be changed by the operation of the operating unit 74. For example, the examiner operates the mouse 74a and selects a scan line at a position of a tomographic image where he/she desires to check. In response to this, the control unit 70 may change the display to a tomographic image acquired over the selected scan line.

Hereinafter, a method for capturing a tomographic image will be described. As illustrated in FIG. 3, a tomographic and a front image are displayed on the same screen. The examiner uses the front image on the monitor 75, which is observed in real time, and sets the examiner's desired photographing position of a tomographic image. At this point, the examiner moves the target 25 over the front image by a drag operation using the mouse 74a. Consequently, the examiner sets scan positions (photographing positions).

If the examiner moves the target 25 over the front image 20, the control unit 70 sets the scan positions at any time. The control unit 70 then acquires tomographic images at the scan positions. The acquired tomographic images are then displayed on the display screen of the monitor 75 at any time. Moreover, the control unit 70 changes the scan positions of the measurement light in response to an operation signal output from the mouse 74a. The control unit 70 displays the target 25 at a position on the monitor 75, the position corresponding to the changed scan positions. With the change in the scan positions, the scan pattern can be changed by making a selection from a scan pattern setting field 35 with the operating unit 74.

The examiner sets the scan pattern, the scan positions, and the like, and selects an unillustrated photographing switch. In response to this, the control unit 70 acquires a front image and a tomographic image based on the set scan positions.

The control unit 70 stores in the memory 72 a front image acquired at the start of image capture by the multi-scan and information on the scan positions of the multi-scan set on the front image. The front image is used upon tracking control at the time of image recapture (the details are described below).

The control unit 70 controls the optical scanner 108 to obtain a tomographic image of a portion of the fundus, the portion corresponding to the display position of the target 25 on the front image 20 and accordingly scans the fundus with measurement light. The relationship between the display position of the target 25 (the coordinate position on the monitor 75) and the scan position of measurement light by the optical scanner 108 is predetermined. Hence, the control unit 70 drives (controls) the two galvanometer mirrors of the optical scanner 108 as appropriate to scan a scan range corresponding to the set display position of the target 25 with measurement light.

In the case of image capture that uses the scan pattern configured of a plurality of scans at the time of acquiring tomographic images, the control unit 70 acquires tomographic images in the scans, for example, sequentially from an end. For example, in the case of image capture by the above-mentioned multi-scan, the control unit 70 performs image capture over all the scan lines in the longitudinal direction after completing image capture over all the scan lines in the lateral direction. For example, if performing image capture over the scan lines in the lateral direction, the control unit 70 performs image capture sequentially downward from the scan line located at the top end. In other words, the control unit 70 performs image capture sequentially in the lateral direction from a target 25a at the top end to a target 25b at the bottom end in the lateral direction of the target 25.

At this point, the control unit 70 captures a tomographic image a plurality of times over each scan line. For example, the control unit 70 performs image capture the plurality of times at the position of the target 25a at the top end and then moves the position to a photographing position of the next scan line. For example, the control unit 70 adds and averages a plurality of tomographic images while acquiring the tomographic images over each scan line. Consequently, the control unit 70 acquires the averaged image of each scan line from the plurality of tomographic images of the scan line.

The averaging process will be described here. For example, the control unit 70 adds and averages a plurality of tomographic images acquired by the OCT optical system 100. Consequently, the averaged image is acquired. The control unit 70 sets a tomographic image acquired first at the position of each scan line as a reference image, on a scan line by scan line basis. The control unit 70 detects by image processing displacements between the reference image and a plurality of the other tomographic images for the tomographic images acquired at the position of each scan line. The control unit 70 then determines the suitability of the addition process based on the detection result. In addition, the control unit 70 corrects the displacements between the reference image and the tomographic images, and adds the plurality of tomographic images to the reference image. In the embodiment, the control unit 70 sets a tomographic image acquired first (the latest captured image) as the reference image, but the reference image is not limited to this. For example, the control unit 70 may select a reference image that is referred to in the addition process from a plurality of tomographic images.

The control unit 70 sequentially adds and averages the tomographic images with reference to the reference image. A displacement amount between the tomographic image and the reference image is detected for each tomographic image, and each tomographic image is aligned with the reference image. In other words, the reference image is compared with each tomographic image and the displacement direction and displacement amount of the tomographic image from the reference image are detected by image processing for each tomographic image.

Methods for detecting displacement include various image processing methods (e.g., a method using various correlation functions, a method using a Fourier transform, and a method based on the matching of a feature point).

For example, a predetermined reference image (for example, a first acquired tomographic image) or a target image (a tomographic image except for a reference image) is shifted one pixel by one pixel. The reference image and the target image are subsequently compared. The displacement direction and displacement amount between both data of when both image data are most coincident with each other (when the correlation is the strongest) may be detected. Moreover, it is also possible to use a method for extracting a feature point that is common between the predetermined reference image and the target image, and detecting the displacement direction and displacement amount of the extracted feature point.

In the embodiment, the control unit 70 successively calculates a correlation value while shifting pixels of each front image one by one with respect to the reference image. The larger the correlation value is, the stronger the correlation between images is. The maximum value of the correlation value is one. The control unit 70 then sets as the displacement amount the amount of pixel displacement (the number of pixels displaced) when having the maximum correlation value. Moreover, the control unit 70 calculates the shifted direction as the displacement direction.

The control unit 70 makes a determination using a correlation value calculated upon the detection of displacement. For example, the control unit 70 excludes a tomographic image whose correlation value is smaller than a predetermined threshold value (for example, 0.4) from target tomographic images used for the addition process. In other words, if the correlation value is small, an image capture area is highly likely to be very different between the reference image and the tomographic image due to fine involuntary movement during fixation, a displacement between the apparatus and the eye, or the like. The method for determining whether or not an image is suitable as an image to be used for the addition process is not limited to this. For example, a tomographic image where the detected displacement amount exceeds an allowable range may be excluded from the addition process targets.

As described above, the displacement amount and the displacement direction are detected and accordingly the suitability as an image to be used for the addition process is determined. The control unit 70 then corrects the displacement in an image determined to be suitable as the image for the addition process. The displacement is corrected by shifting by the displacement amount of each tomographic image from the reference image. After the displacement is corrected, the control unit 70 adds a pixel value of the tomographic image to a pixel value of the reference image.

In this manner, a plurality of tomographic images acquired over a plurality of scan lines is added and averaged to improve the quality of the acquired tomographic images.

After the completion of image capture in the lateral direction, the control unit 70 performs image capture over the scan lines in the longitudinal direction as in the image capture in the lateral direction. For example, if image capture is performed over the scan lines in the longitudinal direction, the control unit 70 performs image capture sequentially rightward from the scan line located at the left end. In other words, the control unit 70 performs image capture sequentially in the longitudinal direction from a target 25*c* at the left end to a target 25*d* at the right end in the longitudinal direction of the target 25. The order of image capture is not limited to the above description. For example, the control unit 70 may perform image capture over the scan lines in the lateral direction after completing image capture over the scan lines in the longitudinal direction. Moreover, image capture may be performed alternately over the scan lines in the longitudinal direction and the scan lines in the lateral direction, or image capture over the scan lines in the longitudinal direction and the lateral direction may be switched for each plurality of image captures.

Figure 4:
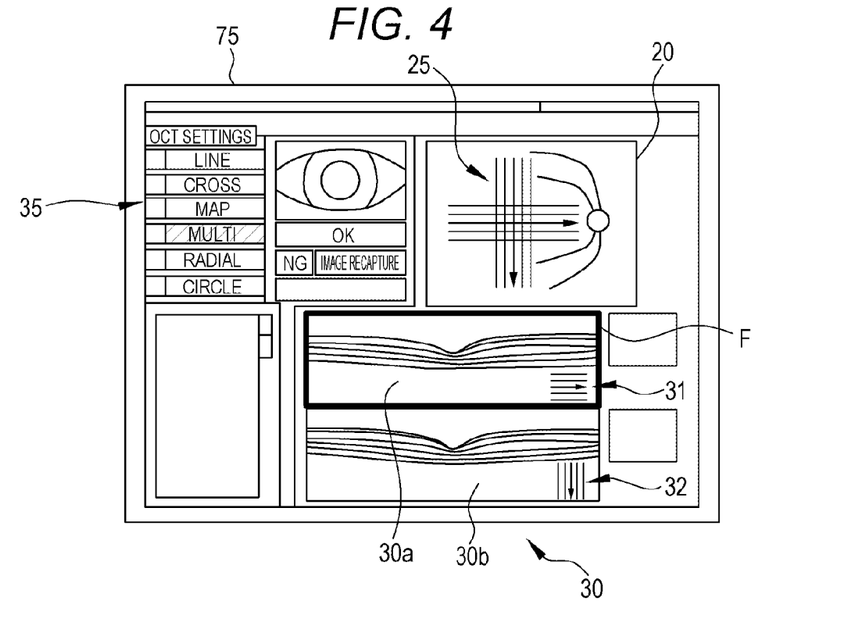
FIG. 4 is an exemplary diagram illustrating a check screen to be displayed on the monitor after image capture by the multi-scan.

As described above, upon the completion of image capture, the control unit 70 stores the acquired tomographic images in the memory 72. The control unit 70 then changes the display on the monitor 75 from the image capture screen to the check screen. FIG. 4 is an exemplary diagram illustrating the check screen to be displayed on the monitor 75 after image capture by the multi-scan. The control unit 70 retrieves the front and tomographic images from the memory 72. The control unit 70 displays the front image 20, the target 25, and the tomographic image 30 on the monitor 75.

For example, the front image 20 displayed on the check screen may be a front image acquired at the start of image capture by the multi-scan. Moreover, for example, tomographic images displayed in the first tomographic image 30*a* and the second tomographic image 30*b* on the check screen may be tomographic images at the center position of the multi-scan, which are of scans in the lateral direction (the first tomographic image) and the longitudinal direction (the second tomographic image). Naturally, images at different scan positions may be displayed as acquired images on the check screen. The tomographic image acquired by the averaging process is displayed on the check screen. At this point, the control unit 70 may display, for example, the number of tomographic images used when adding and averaging the tomographic images of each scan line. Moreover, it may be set such that the number of all tomographic images of each scan line and the number of the averaged tomographic images out of the captured tomographic images are displayed. Moreover, the control unit 70 may assign a number to each scan line, and assign a number similar to each scan line to its corresponding tomographic image to make it possible to understand the correspondence between the tomographic and front images and the scan line.

A scan display 31 is displayed in the first tomographic image 30*a*. The scan display 31 shows a scan line at a position where the first tomographic image 30*a* on display was acquired out of the plurality scan lines in the lateral direction, the scan lines configuring the multi-scan. For example, if the first tomographic image 30*a* is a tomographic image acquired at a sectioning position that passes through the center position 26 of the target 25 in the lateral direction, the scan display 31 is displayed so as to show a scan line at the center position out of the plurality of scan lines in the lateral direction. Moreover, a scan display 32 is displayed in the second tomographic image 30*b*. The scan display 32 shows a scan line at a position where the second tomographic image 30*b* on display was acquired out of the plurality of scan lines in the longitudinal direction, the scan lines configuring the multi-scan.

The examiner checks whether or not image capture over each scan line is well completed. For example, the examiner operates the mouse 74*a*, moves an unillustrated pointer (for example, an arrow or a cross mark) on the monitor 75, and selects the first tomographic image 30*a* or the second tomographic image 30*b*. If the tomographic image is selected, the control unit 70 displays a frame F so as to surround the selected tomographic image. In this state, the examiner uses the mouse 74*a* for a scroll operation and accordingly the tomographic image displayed is changed from the tomographic image on display to another tomographic image. For example, it is assumed that the tomographic image at the center position out of the tomographic images captured over the scan lines in the lateral direction is displayed in the first tomographic image 30*a*. In this case, if the examiner performs the scroll operation, the tomographic image displayed in the first tomographic image 30*a* is changed to a tomographic image captured at the scan line position located above or below the center position. Moreover, with the change in the display of the tomographic image, the display of the scan displays 31 and 32 showing the acquisition positions of the tomographic images is changed to the display showing the scan line positions corresponding to the changed tomographic images.

In the embodiment, a tomographic image displayed is changed by the scroll operation. The embodiment is not limited to this, but, for example, all captured tomographic images may be listed and displayed.

Figure 5:
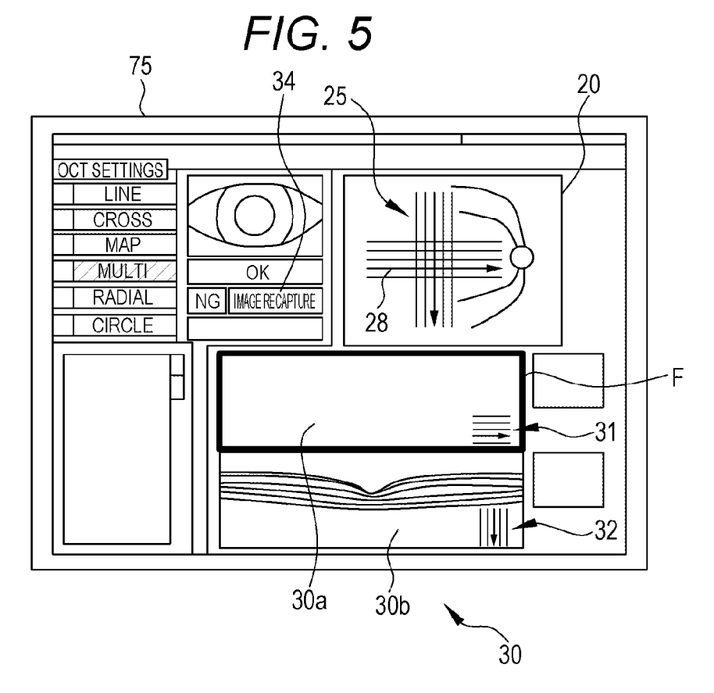
FIG. 5 is an exemplary diagram illustrating the check screen to be displayed on the monitor after changing a tomographic image of a first tomographic image.

FIG. 5 is an exemplary diagram illustrating the check screen to be displayed on the monitor 75 after changing the tomographic image of the first tomographic image 30*a*. For example, it is assumed that a tomographic image acquired at the position of a scan line 28 was not captured and acquired well. In this case, as illustrated in FIG. 5, the first tomographic image 30*a* does not display an excellent tomographic image. In this manner, the examiner changes the first tomographic image 30*a* and the second tomographic image 30*b* and checks the acquired tomographic images. Consequently, the examiner can check whether or not image capture was performed well.

It is assumed that the examiner has checked the scan line where image capture was not performed well as a result of operating the mouse 74a and checking the tomographic images of the scan lines. In this case, the examiner can perform image recapture at this particular scan line position. In the following description of image recapture, a case where image capture was not performed well at the position of the scan line 28 is taken as an example.

For example, the examiner operates the mouse 74a, checks the tomographic images, and selects the scan line where image recapture is performed. For example, if the scan line 28 where image capture was not performed well is selected, the control unit 70 changes the color of the selected scan line 28 in the target 25 (the color change is not illustrated in FIG. 5). The embodiment is not limited to this, but it is sufficient if a selected scan line is displayed to be different from unselected scan lines. For example, the size, shape, or the like of the scan line may be changed.

When completing the selection of the scan line 28 where image recapture is performed, the examiner selects a rephotographing switch 34. The control unit 70 changes the display on the monitor 75 from the check screen to the image capture screen to perform image recapture at the photographing position of the selected scan line 28. In the embodiment, image recapture is performed over one scan line. The embodiment is not limited to this, but the examiner can also select a plurality of scan lines where image recapture is performed all together. In this case, for example, the plurality of scan lines is selected, and the selected scan lines are set as candidates of image recapture. If the rephotographing switch 34 is selected, then the control unit 70 performs image recapture at positions corresponding to all the tomographic images set as the candidates.

Figure 6:
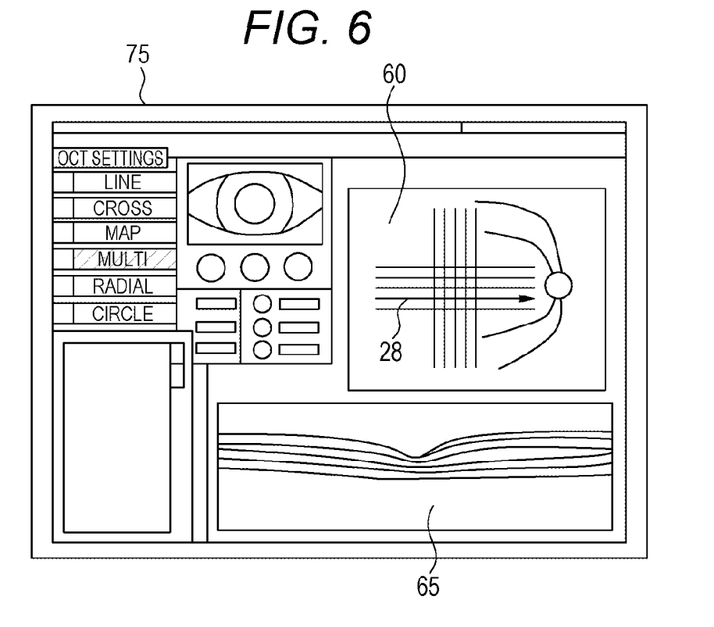
FIG. 6 is an exemplary diagram illustrating the image capture screen to be displayed on the monitor at the time of image recapture.

FIG. 6 is an exemplary diagram illustrating the image capture screen to be displayed on the monitor 75 at the time of image recapture. For example, a front image 60 and a tomographic image 65 are displayed on the monitor 75. A front image that is currently being acquired is displayed in the front image 60. A tomographic image that has been acquired at the position of the scan line 28 selected as the scan line where image recapture is performed is displayed in the tomographic image 65.

At this point, it is assumed that the front image is displaced from the scan position (photographing position) due to the fine involuntary movement of the examinee's eye, or the like. In this case, the scan position is corrected to acquire a tomographic image at the same position as the position set as the scan position. For example, image capture may be performed at different photographing positions between the position of the scan line 28 upon the past image capture by a multi-scan or the like and the position of the scan line 28 upon image recapture. Hence, the control unit 70 performs the tracking control.

Hereinafter, the tracking control will be described. The control unit 70 corrects the scan position upon image recapture by using a front image acquired at the start of image capture by a multi-scan, the front image being stored in the memory 72, and information on the scan positions of the multi-scan, the scan positions being set on the front image. The control unit 70 compares the front image stored in the memory 72 and a current front image first. The control unit 70 detects (computes) by image processing the displacement direction and displacement amount of the current front image from the front image acquired at the start of image capture by the multi-scan.

The control unit 70 sets the front image data acquired at the start of image capture by the multi-scan as the reference image and calculates a displacement between the reference image and a front image acquired in real time. Consequently, information on the displacement from the front image acquired at the start of image capture by the multi-scan can be obtained.

As described above, if the displacement is detected, the control unit 70 corrects the displacement between the position of the scan line 28 upon the past image capture and the position of the scan line 28 upon image recapture. The correction is made by controlling the drive of the two galvanometer mirrors of the optical scanner 108 as appropriate. Consequently, the scan position is corrected. In this manner, even if the examinee's eye is shifted, the scan position is corrected. Consequently, the control unit 70 is enabled to acquire a tomographic image at the same position as the position set as the scan position.

It is assumed here that the examiner has selected the photographing switch (not illustrated). The control unit 70 then acquires a tomographic image at the position of the scan line 28 and stores the tomographic image in the memory 72. When image recapture is performed at positions of a plurality of scan lines, if the photographing switch is selected, image recapture is performed sequentially over the scan lines.

In the embodiment, the control unit 70 corrects a displacement by controlling the drive of the two galvanometer mirrors of the optical scanner 108 as appropriate. The embodiment is not limited to this, but the control unit 70 may wait for image capture until the reference image agrees with a front image acquired in real time and the displacement disappears. In this case, when the reference image agrees with the front image acquired in real time, image capture may be performed. Alternatively, their agreement may be notified to notify the examiner of the time to start image capture.

In the tracking control, various image processing methods (a method that uses various correlation functions, a method that uses the Fourier transform, a method based on feature point matching, and the like) can be used as the method for detecting a displacement between two images as in the above averaging process.

Figure 7:
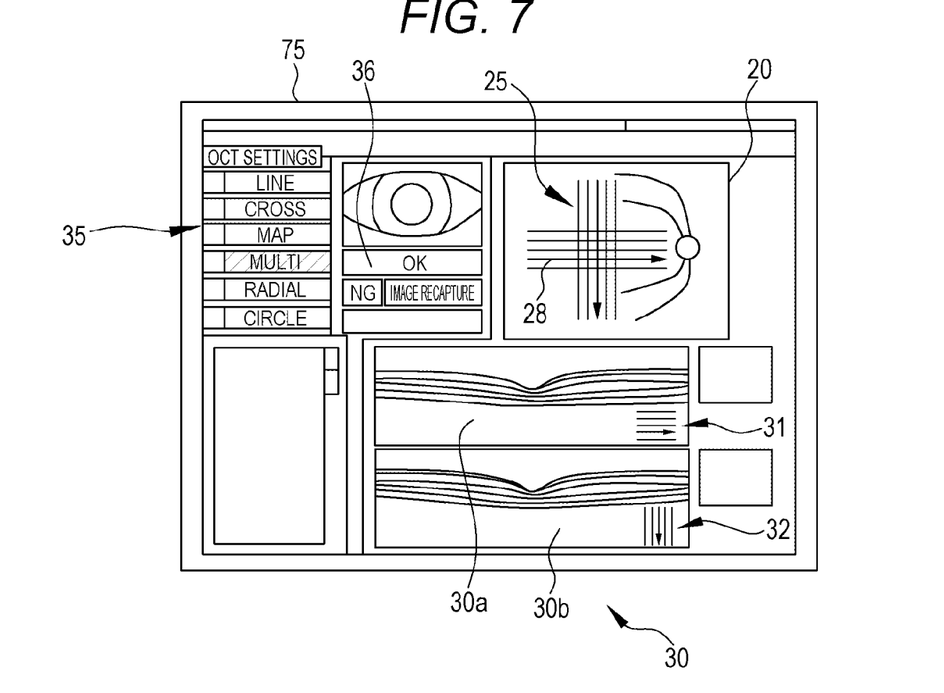
FIG. 7 is an exemplary diagram illustrating the check screen to be displayed on the monitor after the image recapture.

As described above, when image recapture is complete, the control unit 70 changes the display on the monitor 75 from the image capture screen to the check screen. FIG. 7 is an exemplary diagram illustrating the check screen to be displayed on the monitor 75 after image recapture. The control unit 70 replaces tomographic image data before the image recapture with tomographic image data obtained by the image recapture. In other words, the control unit 70 changes the tomographic image at the photographing position (transverse position) of the scan line 28 selected as the scan line where image recapture was performed to the tomographic image acquired at the time of the image recapture. Consequently, as illustrated in FIG. 7, the tomographic image corresponding to the photographing position of the scan line 28 is displayed in the first tomographic image 30a. Consequently, all tomographic images of the scan lines acquired by the multi-scan become excellent.

In the embodiment, the control unit 70 replaces tomographic image data obtained by image recapture with tomographic image data before the image recapture. The embodiment is not limited to this, but the control unit 70 may, for example, add and average tomographic image data obtained by image recapture and tomographic image data before the image recapture to acquire an excellent tomographic image.

Figure 8:
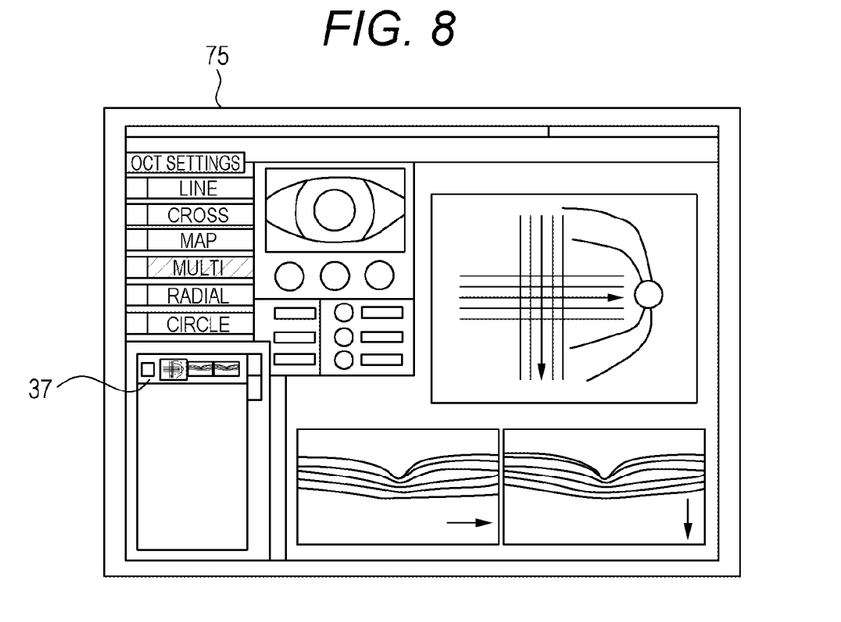
FIG. 8 is an exemplary diagram illustrating the image capture screen to be displayed on the monitor after completing image capture.

When confirming that the tomographic images of all the scan lines in the multi-scan have been well captured after completing the image recapture, the examiner selects a photographing completion switch 36. If the photographing completion switch 36 is selected, the control unit 70 changes the display on the monitor 75 from the check screen to the image capture screen, which enables the next image capture. FIG. 8 is an exemplary diagram illustrating the image capture screen to be displayed on the monitor 75 after completing image capture. The control unit 70 displays image capture data of image captures completed in a photographing completion list 37. The examiner selects from the photographing completion list 37 image capture data to maintain a state of being stored in the memory 72, the image capture data being used for analysis and the like. Alternatively, image capture data to be deleted from the memory 72 is selected. For example, the examiner selects the image capture data that he/she desires to save in the memory 72 and selects a decision switch (not illustrated). In image recapture, the examiner may select an image capture for which image recapture is performed from the photographing completion list 37. In this case, the examiner selects, by a click operation or the like, the image capture for which image recapture is performed from the photographing completion list 37. The control unit 70 retrieves data on the selected image capture from the memory 72 and displays its check screen. Consequently, it becomes possible to select on the check screen a scan line over which image recapture is performed and to perform image recapture.

If the decision switch is selected, the control unit 70 ends the image capture. The display on the monitor 75 then changes from the check screen to an analysis screen. Analysis results of the tomographic images (for example, a layer detection result and a layer thickness map), as well as the acquired images, are displayed on the analysis screen. The examiner checks the analysis results and performs the settings of a diagnosis of a lesion and the like, follow-up image capture, and the like.

As described above, the control unit 70 performs image capture in the scan pattern formed of a combination of the plurality of scans. Consequently, it becomes possible to perform image capture only at a photographing position where it is desired to perform image recapture. Hence, the time for image recapture can be shortened. Moreover, at the time of image recapture, a tomographic image at the same photographing position (transverse position) can be accurately captured by the tracking control.

<Modification>

In the embodiment, at the time of image recapture, the examiner can change photographing conditions (for example, scan conditions). The operating unit 74 is operated to change the photographing conditions. Hereinafter, the changes in the photographing conditions will be described taking changes in the scan conditions as an example. The changes in the scan conditions include changes in scan length (scan width), the pattern of a scan (scan pattern), and the rotation angle of a scan pattern (a line is rotated around a scan center). If the scan conditions are set, the control unit 70 compares a front image acquired in advance (the reference image) with a current front image. The control unit 70 subsequently detects (computes) by image processing the displacement direction and displacement amount of the current front image from the reference image.

For example, if changing the scan pattern, the examiner operates the mouse 74a and selects a desired scan pattern from the scan pattern setting field 35 displayed on the monitor 75. Consequently, the scan pattern is changed. Various scan patterns are listed in the scan pattern setting field 35. For example, the scan patterns include a cross (cross) scan, a circle scan, a raster scan, and a radial scan.

Assume that the examiner operates the mouse 74a and selects a predetermined scan pattern in the scan pattern setting field 35 displayed on the monitor 75. In this case, the control unit 70 changes the scan pattern to the selected scan pattern. At this point, a scan center position is preset for each scan pattern. The control unit 70 changes the scan pattern such that a scan center position of a past scan pattern agrees with a scan center position of the selected scan pattern. If the scan position is not changed, a tomographic image related to the same (or substantially the same) portion on the fundus is acquired in a different scan pattern.

The control unit 70 continues tracking (tracking control) even after the above change in scanning condition. If the scanning condition is changed, the control unit 70 compares the front image used for the correction (tracking) of the scan position before the change in scanning condition with a current front image. The control unit 70 detects (computes) displacement of the current front image from the front image, by image processing. After the displacement is detected, the control unit 70 drives (controls) the two galvanometer mirrors of the optical scanner 108 as appropriate to eliminate the displacement of the scan position on the changed scanning condition (second scanning condition) so as to correct the displacement of the scan position after the change in scanning direction. Consequently, the scan position after the change in scanning condition is correct.

When the scan condition is changed at the time of image recapture, the control unit 70 may perform image recapture on a plurality of scan conditions. In this case, image capture is performed sequentially on the set scan conditions, and tomographic images are acquired.

When selecting the photographing position at the time of image recapture, the control unit 70 displays a tomographic image constructed in response to an interference signal acquired in a predetermined scan pattern before the image recapture. In addition, the control unit 70 may reconstruct a tomographic image in a different scan pattern in response to the acquired interference signal to display the tomographic image. For example, the control unit 70 not only displays a tomographic image acquired by a raster scan but also constructs and displays a tomographic image in a circle scan in response to the interference signal acquired by the raster scan. In other words, the control unit 70 constructs and displays a tomographic image in a different scan pattern from a common interference signal. In this case, the examiner can check tomographic images related to a desired portion in more patterns. This is useful when a portion where image recapture is performed is selected.

In the embodiment, the scan condition is taken as an example of the photographing condition to be changed at the time of image recapture. The embodiment is not limited to this, but another photographing condition may be changed at the time of image recapture. For example, if the examinee's eye is not fixated stably at the time of image recapture, fixation target conditions (for example, the pattern of a fixation target, the size of a fixation target, and the position of a fixation target) may be changed.

In this manner, the embodiment can change the scan condition at the time of image recapture. Hence, when the scan condition is changed, it is not necessary to adjust the scan position again. Hence, tomographic images at the same portion (for example, a lesioned part) of the fundus can be easily acquired in various scan patterns, which saves the examiner time and trouble. Moreover, it is possible to prevent a different portion of the fundus from being set as the scan position, which ensures accurate scanning. Moreover, it is possible to change the scan pattern to one corresponding to the image capture portion without the scan position being displaced from the same portion. Accordingly, convenience is improved. Moreover, if observing a tomographic image acquired by an image capture before image recapture and desiring to capture a detailed image of a predetermined target portion, the examiner can select an area whose detailed image is desired to be captured, and capture images of the portion in different scan patterns. Hence, more detailed information on the selected portion can be acquired from the acquired various tomographic images.

In the embodiment, a scan line is selected when image recapture is performed. The embodiment is not limited to this, but, for example, a tomographic image may be selected instead of a scan line. For example, when a tomographic image is selected, a tomographic image surrounded by the frame F may be treated as the selected tomographic image. The tomographic image may be selected by the click operation of the mouse 74a. At this point, for example, the control unit 70 may set the tomographic image selected by the click operation as an image recapture candidate. If the rephotographing switch 34 is subsequently selected, the control unit 70 may perform image recapture at positions corresponding to all the tomographic images set as the candidates. Moreover, the tomographic image may be selected and recaptured by a double click operation. Moreover, the color of a scan line corresponding to the selected tomographic image may be changed at the time of the selection of the tomographic image. Moreover, when a tomographic image set for image recapture is being displayed, the control unit 70 may display the color of the frame F in a different color from that of an unselected tomographic image.

Moreover, when a scan line where image recapture is performed is selected, an image created in response to an interference signal may be used. For example, the control unit 70 acquires an OCT front image in response to an interference signal acquired by a raster scan formed of a plurality of line scans in the lateral direction. The OCT front image is acquired based on a tomographic image. Hence, positions of the OCT front image are associated with tomographic images acquired by OCT. In this case, for example, the examiner may check the OCT front image, select a scan line of a portion where the data of the OCT front image is not displayed, and perform image recapture. There is a method, as a method for acquiring an OCT front image, for scanning measurement light two-dimensionally, and adding the spectral intensities of interference signals from the light receiving device on the X and Y points.

At the time of a raster scan, the control unit 70 performs a raster scan, subsequently performs a line scan in the longitudinal direction to acquire its tomographic image. Consequently, the examiner checks the tomographic image acquired by the line scan in the longitudinal direction and accordingly can easily check a photographing position where the tomographic image could not be acquired well among the photographing positions of a plurality of line scans in the lateral direction. In other words, the examiner may select a scan line so as to check a missed portion of data in the tomographic image acquired by a line scan in the longitudinal direction and recapture the portion.

Moreover, a scan line where image recapture is performed may be selected based on image capture information. For example, the image capture information may be information on the averaging process, the layer detection result of a tomographic image, brightness information of a tomographic image, and/or the like. For example, the examiner selects a scan line having a small number of images from the number of averaged images of tomographic images used for the averaging process displayed for each scan line, and performs image recapture. Moreover, for example, the brightness information of a tomographic image is displayed for each scan line. The examiner then selects a scan line having a small luminance value and performs image recapture. The scan lines may be displayed in different, colors on the monitor 75 according to the values of the image capture information. For example, the control unit 70 may display a scan line where the number of averaged images is less than a predetermined threshold value in red while displaying a scan line where the number of averaged images is equal to or more than the predetermined threshold value in green.

In the embodiment, the examiner checks tomographic images and the like and selects a scan line where image recapture is performed. The embodiment is not limited to this, but the control unit 70 may extract a scan line where image recapture should be performed based on a predetermined condition and present the scan line to the examiner. For example, the control unit 70 may extract a scan line where the number of images did not reach a predetermined number from the number of tomographic images used for the averaging process for each scan line. Moreover, the control unit 70 may acquire the brightness information of a tomographic image and extract a scan line where the luminance value does not satisfy a predetermined threshold value as a scan line where image recapture should be performed. Consequently, the time and trouble of the examiner is reduced and image recapture can be performed smoothly. Moreover, image recapture can be appropriately performed without the fear of a mistake that the examiner forgets to select a tomographic image that should be recaptured.

In the embodiment, when a plurality of tomographic images is captured at a photographing position in each scan line, the tracking control may be performed. In this case, the control unit 70 compares a front image acquired at the start of image capture with a current front image acquired at any time during image capture. The control unit 70 detects (computes) by image processing the displacement of the current front image from the front image at the start of image capture based on the comparison result. If the displacement is detected, the control unit 70 controls the drive of the two galvanometer mirrors of the optical scanner 108 as appropriate so as to eliminate the displacement of the scan position after a change in the scan condition. Consequently, tomographic images of the same portion can be accurately captured over the plurality of scan lines. Consequently, the number of tomographic images that can be used for the averaging process is increased. Hence, the quality of a tomographic image acquired is improved. Moreover, the possibility of capturing a different portion from a photographing position selected by the examiner is reduced. Hence, the number of acquisition errors of tomographic images is reduced.

In the embodiment, the control unit 70 or the examiner may set a rephotographing position in a predetermined area. For example, if desiring to select a plurality of adjacent line scans of tomographic images captured by a raster scan, the examiner selects a predetermined area on a front image by the drag operation of the mouse 74a. The control unit 70 may then recapture the tomographic images over scan lines included in the selected area.

In the embodiment, the optical tomography apparatus that captures the fundus has been described as the ophthalmologic photographing apparatus. The present disclosure is not limited to this, but can also be applied to an optical tomography apparatus that captures a tomographic image of the anterior segment.

The present disclosure is not limited to the apparatus disclosed in the embodiment. For example, ophthalmologic photographing software (program) that performs the functions of the present apparatus (the control unit 70) illustrated in the embodiment may be provided to the system or apparatus via a network or various recording media. A computer (for example, a CPU) of the system or apparatus can also read and execute the program.

The ophthalmologic photography represented in the present embodiment can be performed not only by the present apparatus but also by another apparatus. Moreover, for example, software (program) for causing another computer to perform a process to be performed by the control unit 70 of the present apparatus can be supplied to a system or device via a network or various recording media. In this case, a computer (e.g., CPU or the like) of the system or device reads the program to execute the process.

Moreover, in the embodiment, substantially all the processes in the present device may be controlled by the control unit 70. Moreover, a program (ophthalmologic program) for performing these processes may be recorded in a recording medium such as the memory 72. Furthermore, an information processing device (e.g., a computer) that can read the program may be used instead of the control unit 70.

In this configuration an arithmetic unit (CPU or MPU) of the information processing device reads the program recorded in the recording medium and executes the processes. Therefore, it can be said that the program itself realizes the processes.

As the above information processing device, in addition to a general computer (e.g., a workstation or personal computer), a function expansion board or function expansion unit that is attached to a computer can be used.

Moreover, the above program includes program codes (an executable program, an intermediate code program, a source program, and the like) of software that realizes the processes. The program may be used singly or in combination with another program (such as an OS). Moreover, the program may be read from a recording medium, then recorded once in memory (such as RAM) in the device, and subsequently read again to be executed.

Moreover, a recording medium in which the program is recorded may be one that can be separated readily from the information processing device, or one that is fixed (attached) to the device. Furthermore, a recording medium may be one that is connected to the device as an external storage device.

A magnetic tape such as a video tape or cassette tape, a magnetic disk such as a floppy (registered trademark) disk, MD, or hard disk, a magneto-optical disk such as an MO, an optical disc such as a CD, DVD or BD, a memory card such as an IC card or optical card, a semiconductor memory such as a Mask ROM, EPROM, EEPROM, flash ROM, or USB memory, or the like can be applied as such a recording medium.

Moreover, a recording medium that is connected to the information processing device via networks (an intranet, the Internet, and the like) can be used. In this case, the information processing device acquires the program by downloading via a network. In other words, the above program may be acquired via a transmission medium (a medium holding the program in flux) such as a network (one that is connected to a wired or wireless channel). It is preferable that a program for download should previously be stored in the information processing device (or in a transmitting side device/receiving side device). Moreover, the above recording medium is a non-transitory (non-transitory) medium.

In the state where the check screen is being displayed, the control unit 70 can perform image recapture smoothly by executing at least any of the tracking control of the measurement light and the adjustment of the optical path length in accordance with the movement of the examinee's eye. The application of the measurement light may be stopped on purpose during the check screen to reduce the burden on the examinee's eye. After image recapture, for example, the control unit 70 may replace an interference signal at a transverse position selected before the image recapture in response to an operation signal from the operating unit 74 for an image on the monitor 75 with an interference signal acquired at a rephotographing transverse position. Moreover, for example, the control unit 70 may add and average the interference signal at the transverse position selected before the image recapture in response to the operation signal from the operating unit 74 for the image on the monitor 75 and the interference signal acquired at the rephotographing transverse position.

Moreover, the ophthalmologic photographing apparatus according to the embodiment may be the following first to seventh ophthalmologic photographing apparatuses. The first ophthalmologic photographing apparatus includes: an optical coherence system configured to obtain a tomographic image of an examinee's eye, having an optical scanner configured to scan light emitted from a light source over the examinee's eye and a detector configured to detect an interference signal of measurement light and reference light, which are emitted from the light source; an observing optical system configured to acquire a front image of the examinee's eye; a controller configured to control the optical scanner at a plurality of different transverse positions on the examinee's eye set on the front image, scan the measurement light, and acquire the interference signals at the respective transverse positions; a display controller configured to display on a monitor images created in response to the interference signals at the respective transverse positions, the interference signals having been acquired by the controller; and an image recapture setting unit configured to set at least one or more rephotographing transverse positions in response to an operation signal from an operating unit for the images on the monitor, and the controller scans the measurement light at the rephotographing transverse position set by the image recapture setting unit to acquire the interference signal.

In the second ophthalmologic photographing apparatus according to the first ophthalmologic photographing apparatus, the controller detects by image processing a displacement between a first front image of the examinee's eye acquired by the observing optical system upon the acquisition of the interference signals at the plurality of different transverse positions and a second front image acquired by the observing optical system upon the acquisition of the interference signal at the rephotographing transverse position set by the image recapture setting unit, controls the drive of the optical scanner based on the detection result to acquire the interference signal at the rephotographing transverse position set by the image recapture setting unit.

The third ophthalmologic photographing apparatus according to the first ophthalmologic photographing apparatus replaces the interference signal at the transverse position selected before image recapture in response to the operation signal from the operating unit for the image on the monitor with the interference signal acquired by the controller at the rephotographing transverse position set by the image recapture setting unit, or adds and averages the interference signal of the transverse position selected before image recapture in response to the operation signal from the operating unit for the image on the monitor and the interference signal acquired by the controller at the rephotographing transverse position set by the image recapture setting unit.

In the fourth ophthalmologic photographing apparatus according to the first ophthalmologic photographing apparatus, the display controller displays an image capture screen for acquiring the interference signal and a check screen for checking the acquired interference signal, the controller controls on the image capture screen the optical scanner at the plurality of different transverse positions on the examinee's eye set on the front image, scans the measurement light to acquire the interference signals at the respective transverse positions, the display controller displays the images created in response to the interference signals at the respective transverse positions, the interference signals having been acquired by the controller, on the check screen on the monitor, the image recapture setting unit sets at least the one or more rephotographing transverse positions in response to the operation signal from the operating unit for the images on the monitor, and the controller scans the measurement light at the rephotographing transverse position set by the image recapture setting unit to acquire the interference signal on the image capture screen.

In the fifth ophthalmologic photographing apparatus according to the first ophthalmologic photographing apparatus, the image recapture setting unit sets at least the one or more rephotographing transverse positions in response to the operation signal from the operating unit for the images in the still state on the monitor.

In the sixth ophthalmologic photographing apparatus according to the fifth ophthalmologic photographing apparatus, the image created in response to the interference signal is at least any of a front image and a tomographic image.

In the seventh ophthalmologic photographing apparatus according to the sixth ophthalmologic photographing apparatus, the image recapture setting unit sets a transverse position on a front image with reference to a tomographic image selected in response to an operation signal from the operating unit as the rephotographing transverse position for the tomographic image in the still state on the monitor.

Moreover, the ophthalmologic photographing program according to the embodiment may be the following first ophthalmologic photographing program.

The first ophthalmologic photographing program is an ophthalmologic photographing program to be executed by a control apparatus that controls the operation of an ophthalmologic photographing apparatus including an optical coherence system configured to obtain a tomographic image of an examinee's eye, having an optical scanner to scan light emitted from a light source over the examinee's eye and a detector configured to detect an interference signal of measurement light and reference light, which are emitted from the light source, and an observing optical system configured to acquire a front image of the examinee's eye, and the ophthalmologic photographing program is executed by a processor of the control apparatus to cause the control apparatus to execute: a control step of controlling the optical scanner at a plurality of different transverse positions on the examinee's eye set on the front image acquired by the observing optical system, scanning the measurement light, and acquiring the interference signals at the respective transverse positions; a display control step of displaying on a monitor images created in response to the interference signals at the plurality of different transverse positions, the interference signals having been acquired in the control step; an image recapture setting step of setting at least one or more rephotographing transverse positions in response to an operation signal from an operating unit for the images on the monitor; and an image recapture control step of scanning the measurement light at the rephotographing transverse position set in the image recapture setting step and reacquiring the interference signal.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ophthalmologic photographing apparatus comprising:
    an optical coherence system configured to obtain a tomographic image of an examinee's eye, including an optical scanner configured to scan the examinee's eye with measurement light and a detector configured to detect an interference signal of the measurement light and reference light;
    an observing optical system configured to acquire a front image of the examinee's eye;
    a scan controller configured to control the optical scanner to scan with the measurement light a plurality of different transverse positions set on the front image, and acquire first interference signals at the respective transverse positions;
    a display controller configured to display on a monitor an image created in response to the first interference signal; and
    an image recapture setting unit configured to set a rephotographing transverse position in response to an operation signal from an operating unit for the image on the monitor, wherein
    the scan controller scans the examinee's eye with the measurement light at the rephotographing transverse position to acquire a second interference signal.

2. The ophthalmologic photographing apparatus according to claim 1, wherein
    the observing optical system is configured to acquire a first front image of the examinee's eye upon the acquisition of the first interference signal, and acquire a second front image of the examinee's eye upon the acquisition of the second interference signal at the rephotographing transverse position, and
    the scan controller is configured to perform image processing to detect a displacement between the first front image and the second front image, control the optical scanner based on the detection result to correct the displacement, and reacquire the second interference signal at the rephotographing transverse position.

3. The ophthalmologic photographing apparatus according to claim 1, wherein the scan controller is configured to replace the first interference signal acquired at the rephotographing transverse position with the second interference signal acquired at the rephotographing transverse position.

4. The ophthalmologic photographing apparatus according to claim 1, wherein
    the scan controller is configured to add and average the first interference signal acquired at the rephotographing transverse position and the second interference signal acquired at the rephotographing transverse position.

5. The ophthalmologic photographing apparatus according to claim 1, wherein
   the display controller is configured to display on the monitor both an image capture screen for acquiring the first interference signal and a check screen for checking the image created in response to the first interference signal, and
   the image recapture setting unit is configured to set the rephotographing transverse position in response to the operation signal from the operating unit for the image on the check screen.

6. The ophthalmologic photographing apparatus according to claim 1, wherein
   the image recapture setting unit is configured to set the rephotographing transverse position in response to the operation signal from the operating unit for the image in a still state displayed on the monitor.

7. The ophthalmologic photographing apparatus according to claim 6, wherein
   the still image created in response to the first interference signal is at least any of a front image and a tomographic image.

8. The ophthalmologic photographing apparatus according to claim 7, wherein
   the image recapture setting unit is configured to set as the rephotographing transverse position a transverse position on a front image with reference to a tomographic image selected in response to an operation signal from the operating unit, for the tomographic image in the still state on the monitor.

* * * * *